United States Patent [19]

Jacobs

[11] Patent Number: 5,641,688
[45] Date of Patent: Jun. 24, 1997

[54] IMMUNOASSAY INCLUDING WASHING A SLIDE AT DIFFERENT LOCATIONS

[75] Inventor: Merrit Nyles Jacobs, Fairport, N.Y.

[73] Assignee: Johnson & Johnson Clinical Diagnostics, Inc., Rochester, N.Y.

[21] Appl. No.: 470,100

[22] Filed: Jun. 6, 1995

[51] Int. Cl.$^6$ .................. G01N 33/543; G01N 33/53; G01N 21/00; G01N 31/22

[52] U.S. Cl. .................. 436/518; 436/524; 436/528; 436/529; 436/530; 436/535; 436/538; 436/808; 435/7.1; 435/7.8; 435/962; 435/969; 435/970; 422/56; 422/57; 422/60; 422/63; 422/70; 422/81; 422/110

[58] Field of Search .................. 422/56, 57, 60, 422/63, 70, 81, 110; 435/7.1, 7.8, 7.92, 7.93–7.95, 962, 969, 970; 436/518, 524, 528, 529, 530, 535, 538, 808

[56] References Cited

U.S. PATENT DOCUMENTS

| | | | |
|---|---|---|---|
| 4,517,288 | 5/1985 | Giegel et al. | 435/7 |
| 4,670,381 | 6/1987 | Frickey et al. | 435/7 |
| 4,857,471 | 8/1989 | Salzman et al. | 436/43 |
| 5,047,322 | 9/1991 | Emmons et al. | 435/6 |
| 5,155,024 | 10/1992 | Eikenberry | 435/7.9 |
| 5,174,960 | 12/1992 | Shaw et al. | 422/63 |
| 5,232,663 | 8/1993 | Wilk | 422/56 |

*Primary Examiner*—James C. Housel
*Assistant Examiner*—Bao-Thuy L. Nguyen
*Attorney, Agent, or Firm*—Dana M. Schmidt

[57] ABSTRACT

A method of separating bound labeled indicator from free labeled indicator in a layer of a test element for immunoassay. The method comprises a) depositing sample containing a target immunoanalyte capable of binding to the labeled indicator or to an immobilized antibody in competition with the labeled indicator, onto an exterior surface of a test element in the presence of the labeled indicator and b) adding an amount of wash liquid to the exterior surface to form a pool of the liquid having a meniscus on the surface, the liquid penetrating the surface over an area bounded by a closed intersect edge formed between the pool meniscus and the surface, so that penetrating liquid can push free labeled indicator away from bound labeled indicator in a volume of the layer below the bounded area. The method is improved in that the step b) comprises i) depositing a first amount of wash liquid at a first location on the surface in a pool, (ii) allowing at least a portion of the pool to spread out through a first portion of the test element to wash out free labeled indicator, and then (iii) depositing a second amount of wash liquid at a second location on the surface different from the first location to spread out through a second portion of the test element different from the first portion, so that the intersect edge is displaced over the surface over time and the liquid flowing into the test element at the intersect edge sweeps through more of the target read area than is the case when washing from only the first location, thus reducing background signal due to non-separated free labeled indicator remaining in the volume.

6 Claims, 8 Drawing Sheets

(RAMPED METHOD)

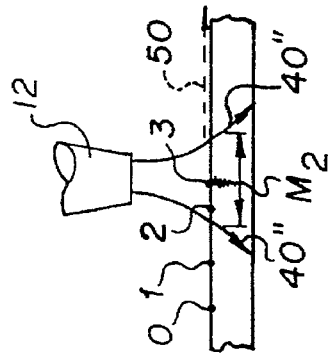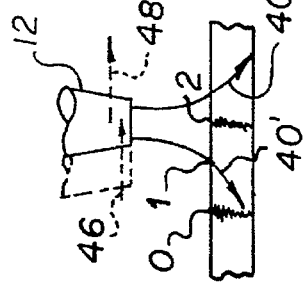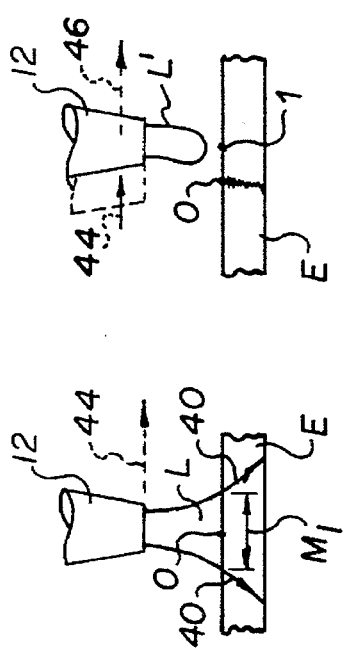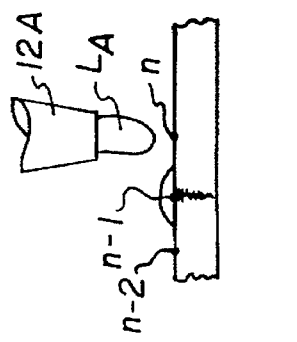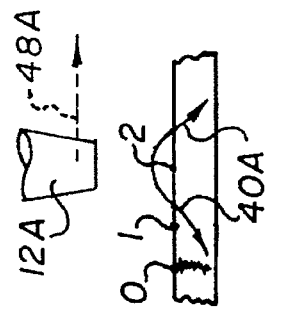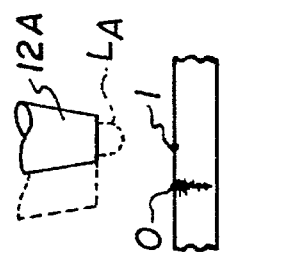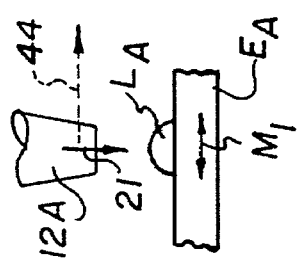

IMMUNOASSAY INCLUDING WASHING A SLIDE AT DIFFERENT LOCATIONS

FIELD OF THE INVENTION

This invention relates to a method of dispensing wash solution onto immunorate slide test elements to achieve improved separation of free labels from bound labels.

BACKGROUND OF THE INVENTION

It is known in immunoassays that the labeled indicator bound or complexed with the antigen analyte must be separated from those that are unbound or "free". When conducting the assay in a slide test element, it is conventional to achieve such bound-free separation by applying a solvent stream, such as water, to the center of the test element while the applicator and test element remain stationary with respect to each other. E.g., in U.S. Pat. No. 4,517,288 the technique is to apply "a stream of a solvent, in which the labeled indicator is soluble, . . . to substantially the center of the reaction zone," col. 5. That there is no relative movement between application and test element is apparent from the fact that "the solvent migrates radially out from the center . . . [and] unbound reactants . . . if visible, would appear as a ring around the reaction zone . . . , ibid.

Such a stationary technique has continued to be the method of choice even in more modern assays, as is apparent from, e.g., the analyzer described in FIG. 11 of U.S. Pat. No. 5,174,960.

I have discovered that such a process of separating bound labeled indicator from free is unsatisfactory, because, in some test elements at least, it tends to leave unseparated free indicators within the center of the washed zone, the same area that is scanned for detection. That is, a staticly disposed stream will leave relatively untouched, the free indicators directly under the center of the impinging stream. The cause of this is the lack of a sufficient fluid flow at the static center, unlike the periphery, effective to sweep the free labeled indicator through the test element. This is because the pool of liquid intersecting a typical spreading layer of a dried test element, will flow rapidly into that layer only around the intersect edge formed by the meniscus of the pool and the surface of the spread layer. Very little flow velocity is experienced under the center of the stream. This is particularly apparent when the sample fluid initially deposited on the surface layer of the porous test element is of higher viscosity levels due to protein, lipids, etc., than the wash liquid, making it more difficult to move or transport the free indicators. Dilution of the sample could reduce this effect, except that dilution of the sample has its own disadvantages, e.g., it reduces concentration of analyte and therefore degrades signal to noise, and adds potential error from the dilution step.

Yet another drawback of a fixed stream is, that it can physically wash away the top layer of the element, such as if that layer is a blush polymer spreading layer.

RELATED APPLICATIONS

Commonly owned U.S. Ser. No. 08/393,632 filed on Feb. 24, 1995 entitled "A Method for Washing Immunoassay Elements" describes one improvement over static wash techniques, namely, a method that varies the rate of dispensing from, first, a rate slower than the absorption rate of the test element, to one that is faster. (Hereinafter that invention is designated as the "ramped" method.) Such method is effective to eliminate the unwashed area that is directly under the tip dispensing the wash. However, I have found that the improvement obtained thereby still leaves only a relatively small area that is uniformly washed. It is desired that a larger area be provided that is fully washed.

SUMMARY OF THE INVENTION

The solution to the above-described problems is to dispense wash in at least two different locations. This can be done by moving the applicator tip, and hence the stream, relative to the test element during wash, so that the "center" of the stream producing the low sweep rate is not confined to one place but also sweeps. As a result, each portion of the test element that is to be washed receives at least part of the time, a faster moving part of the meniscus.

More specifically, there is provided a method of separating bound labeled indicator from free labeled indicator in a layer of a test element for immunoassay, the method comprising a) depositing sample containing a target immunoanalyte capable of binding to the labeled indicator, onto an exterior surface of a test element in the presence of said labeled indicator and b) adding an amount of wash liquid to the exterior surface to form a pool of the liquid having a meniscus on the surface, the liquid penetrating the surface over an area bounded by a closed intersect edge formed between the pool meniscus and the surface, so that penetrating liquid can push free labeled indicator away from bound labeled indicator in a volume of the layer below the bounded area. This method is improved in that step b) comprises i) depositing a first amount of wash liquid at a first location on the surface in a pool, (ii) allowing at least a portion of the pool to spread out through a first portion of the test element to wash out free labeled indicator, and then (iii) depositing a second amount of wash liquid at a second location on the surface different from the first location to spread out through a second portion of the test element different from the first portion, so that the intersect edge is displaced over the surface over time and the liquid flowing into the test element at the intersect edge sweeps through more of the target read area than is the case when washing from only the first location, thus reducing background signal due to non-separated free labeled indicator remaining in the volume.

Accordingly, it is an advantageous feature of the invention that a wash technique is provided that improves the size of the uniformly washed region over that heretofore provided.

It is a related advantageous feature that the dispensing stream, by its movement laterally across the test element, minimizes the impact of the stream upon the top layer that receives it, preventing a physical washing away of that layer.

Other advantageous features will become apparent upon reference to the following Detailed Description, when read in light of the attached drawings.

BRIEF DESCRIPTION OF THE DRAWINGS

FIGS. 3A–D are elevational views similar to that of FIG. 1, illustrating one embodiment of the invention;

FIG. 4A–D are views similar to FIGS. 3A–D, but of a second embodiment;

In FIG. 7, what is displayed is the rate of change of density at each grouped pixel location, the darker gray being indicative, as noted by the associated gray scale color map, with a rate of change that is greater than the lighter grays. In FIGS. 8A and 8B, what is displayed is measured concentrations rather than the first derivative rates.

DESCRIPTION OF THE PREFERRED EMBODIMENTS

Figure 1:
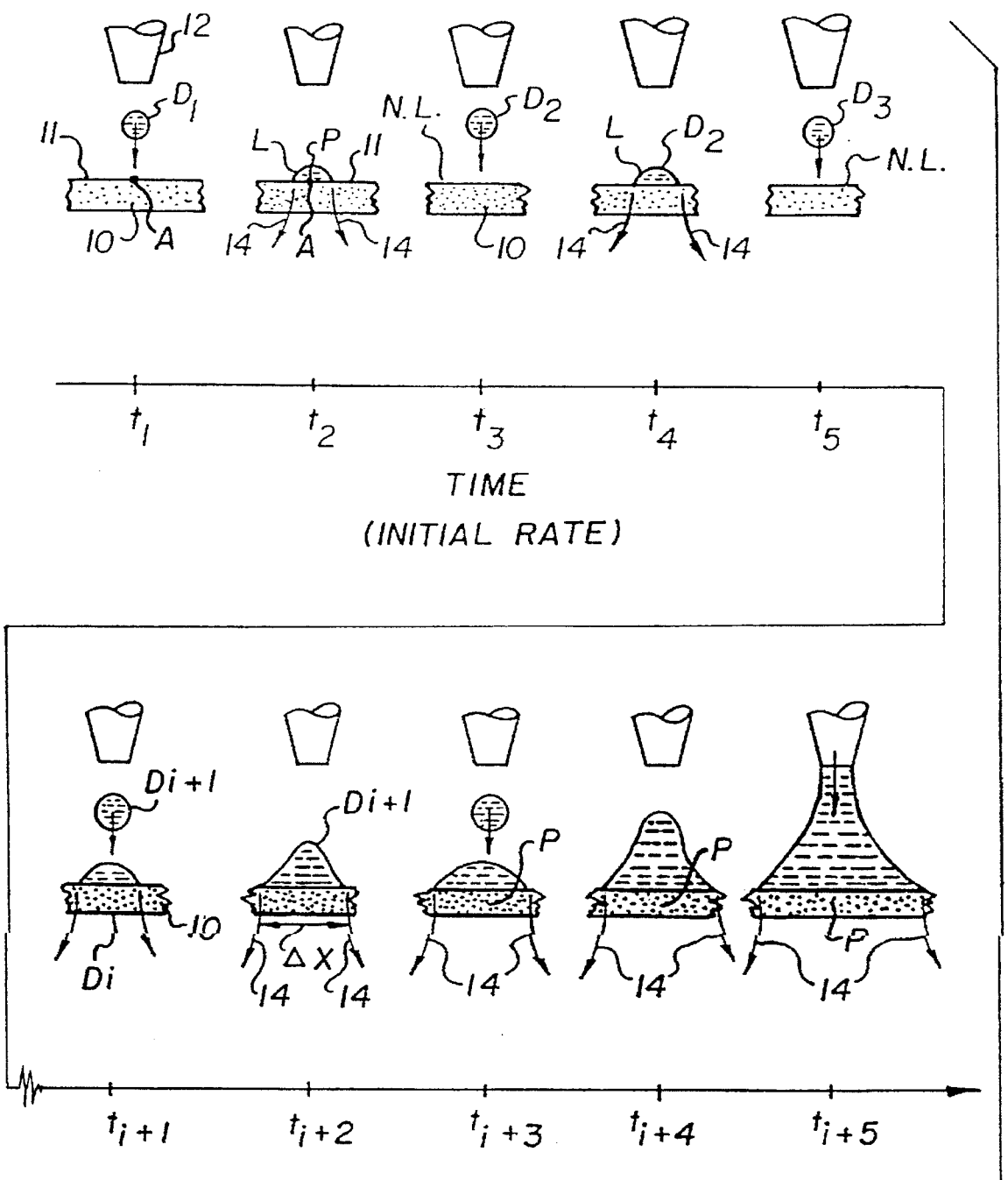
FIG. 1 is a partially schematic elevational view, partially in section, of the dispensing method over time known as the "ramped" method, the subject of the Related Application noted above.

The invention is hereinafter described in connection with certain preferred embodiments, wherein preferred assays are described as being washed with a preferred wash solution, and the method of the wash process is combined with the "ramped" invention described above. In addition, the invention is useful regardless of the assays being washed and the wash liquid composition that is used, and regardless whether the rate of dispensing of wash is the "ramped" method or not. Thus, the invention can also be used with a dispense rate that is always greater than the absorption rate, or always less than the absorption rate, of the slide test element. Still further, the invention is useful with both sandwich-type immunoassays, and competitive types. In the former, the analyte is capable of binding to the labeled indicator to complete the sandwich, while in the latter case, the analyte is capable of binding to an immobilized antibody in competition with a labeled indicator (the target ligand bearing the label).

The process of this invention is particularly useful in low level analyte assays, that is, those having levels below $5 \times 10^{-11}$, for example, CKMB. The advantages achieved include, lower background rates, reduced biases caused by interfering substances, and improved standard deviations.

All washing experiments hereinafter described, were performed on assay elements for phenobarbital, unless otherwise stated. Phenobarbital is a preferred test element for use with this invention, having the following format and composition:

| Phenobarbital Assay Element | | |
|---|---|---|
| Layer | Components | Dry Coverage (g/m²) |
| Gravure | 3',5'-Dichloro-4'-hydroxyacetanilide | 0.00995 |
| | 4,5-Dihydroxy-3-(6,8-disulfo-2-naphthylazo)-2,7-naphthalenedisulfonic acid, sodium salt | 0.0538 |
| | 3-(N-morpholino)propanesulfonic acid | 0.0450 |
| | Bovine serum albumin | 0.00022 |
| | Polyacrylamide | 0.00108 |

| Phenobarbital Assay Element — continued | | |
|---|---|---|
| Layer | Components | Dry Coverage (g/m²) |
| | Triton ™ X-100 Surfactant (Union Carbide) | 0.00430 |
| * | Phenobarbital-horseradish peroxidase conjugate | 0.00001 |
| ** | Modified apo-horseradish peroxidase | 0.01 |
| Spreading Layer | N-[tris(hydroxymethyl)methyl]-2-aminoethanesulfonic acid | 0.219 |
| | Dimedone | 0.50 |
| | 3',5'-Dichloro-4'-hydroxyacetanilide | 0.22 |
| | Vanadyl sulfate | 0.040 |
| | Mannitol | 1.0 |
| | Glycerol | 2.0 |
| | Bovine serum albumin | 1.0 |
| | 4,5-Bis(4-dimethylaminophenyl-2-(3,5-dimethoxy-4-hydroxyphenyl)imidazole | 0.20 |
| | Tetronic ™ T908 surfactant (BASF Corp.) | 0.02 |
| | Surfactant 10G ™ surfactant (Olin Chem. Co.) | 0.248 |
| | Poly(methyl acrylate-co-sodium 2-acrylamido-2-methylpropanesulfonate-co-2-acetoacetoxyethyl methacrylate) | 2.583 |
| | Poly(vinyltoluene-co-methacrylic acid) (~30 μm beads) | 130.0 |
| *** | Polymer particle-antibody conjugate | 0.15 |
| Gel Layer | Gelatin | 10.0 |
| | 3',5'-Dichloro-4'-hydroxyacetanilide | 0.44 |
| | N-[tris(hydroxymethyl)methyl]-2-aminoethanesulfonic acid | 4.58 |
| | Triton ™ x-100 surfactant (Union Carbide) | 0.02 |
| | Bis(vinylsulfonylmethyl) ether | 0.150 |
| | Poly(ethylene terephthalate) support | |

\* The phenobarbital-horseradish peroxidase conjugate employed is that of Example 6 of U.S. Pat. No. 5,298,403 issued March 29, 1994.
\*\* The modified apo-horseradish peroxidase employed is that of Preparation 2 of U.S. SERIAL NO. 277,391 of Roy E. Snoke filed July 19, 1994.
\*\*\* The polymer particle-antibody conjugate employed is poly[styrene-co-3-(p-vinylbenzylthio)propionic acid] (weight ratio 95/5) having an antibody covalently bound thereto.

The basic immunoassay process for such a test element is well understood, so that the following summary suffices: A patient sample (e.g., serum or urine) is deposited onto the test element, a short incubation follows, a portion of the element so deposited with sample is washed, and further incubation follows. Thereafter, a portion of the washed portion is read several times with a densitometer to determine the rate of color development, and this rate is compared to calibrated results that are predictive of the concentration of the analyte—in this case, phenobarbital.

FIG. 1 illustrates the "ramped" method of the related application described above, where tip 12 is stationary over a slide test element 10 that contains the reagents of the assay preincorporated in "dried" form, and to which a sample has been added already. Disposable tip 12 is programmed to dispense drops of wash onto surface 11 of element 10, initially at a rate that is slower than the uptake rate of element 10. The height of the tip 12 above the surface 11 is maintained at a distance appropriate to the size of drops desired. For example, a height of 2.54 mm is preferred for 0.5 microliters.

At time $t_1$, the first drop $D_1$ is dispensed and is shown as "falling" onto the element 10. (Separation need not be such as to produce an actual free-falling drop. The separation and free-fall is shown only to aid in visualization.) Shortly thereafter, at time $t_2$, the drop is on the test element, with a portion of the drop diffusing generally downwardly, arrows 14, before diffusing outwardly, with a meniscus still protruding to form a lens L above the surface 11 of element 10. It is crucial to note that arrows 14 for the wash vector are located mostly at the edge of lens L—very little washing occurs inside of the lens or inside of arrows 14 at center point P. Hence, drops $D_1$ through $D_i$ are preferably of reduced volume (discussed below.)

Before the next drop $D_2$ is released at time $t_3$, most and preferably all, of the lens L of drop $D_1$ is completely absorbed—this is the meaning of a wash dispense rate that is less than the fluid uptake rate of the test element at this time. The complete absorption of $D_1$ is symbolized by the label "N.L." for "no lens". The fluid conditions for drop $D_2$ at time $t_4$ are of course substantially the same as shown for drop $D_1$ at time $t_2$.

By this means, point A is useful for the first time, because the volume under point A is properly washed.

The above described initial rate at less than the fluid uptake rate of the test element provides for a prescribed number of drops "i", which can vary, depending on a number of factors, not the least of which is the drop size. A useful example of the number of repeats "i" is 5 such drops. Because of the need to limit the total wash dispense time to a short duration, e.g., no more than about 60 sec., the maximum time for the dispensing of wash in separate drop format is about 30 sec. Most preferably, it is much less than that, e.g., no more than 18 sec.

The next phase of the ramped method is that in which the rate of dispense of wash exceeds the current uptake rate of the test element—either by an absolute increase in the dispense rate or by reason of the fact that the uptake rate of the test element has declined due to the increased amounts of fluid already present.

Thus, at time $t_{i+1}$ (where $t_i$ is the total time to produce i drops), a drop $D_{i+1}$ is being deposited, while the lens from drop $D_i$ is still present. The effect is, to increase the size of the contact meniscus or lens L of drop $D_{i+1}$ at time $t_{i+2}$. Importantly, this spreads apart the wash diffusion vectors 14 a distance $\Delta x$ so that they become farther and farther apart, through time $t_{i+5}$, as the lens enlarges upon element 10. For this reason, all washing occurs farther and farther from the center point P shown at time $t_{i+3}$. This constitutes an expansion of the diameter of the contact meniscus out to the boundary of the washed portion, at time $t_{i+5}$. Inasmuch as the dispense rate now exceeds the uptake rate of element 10, the liquid buildup on surface 11 is such that, by time $t_{i+5}$, the dispensing becomes a continuous stream rather than individual drops.

It will now be seen that the problem with conventional washes prior to the ramped method has been that they fail to provide the steps occurring through time $t_5$, hence providing insufficient washing in the region of center point P. The ramped method however minimizes that.

THE INSTANT INVENTION

Figure 2:
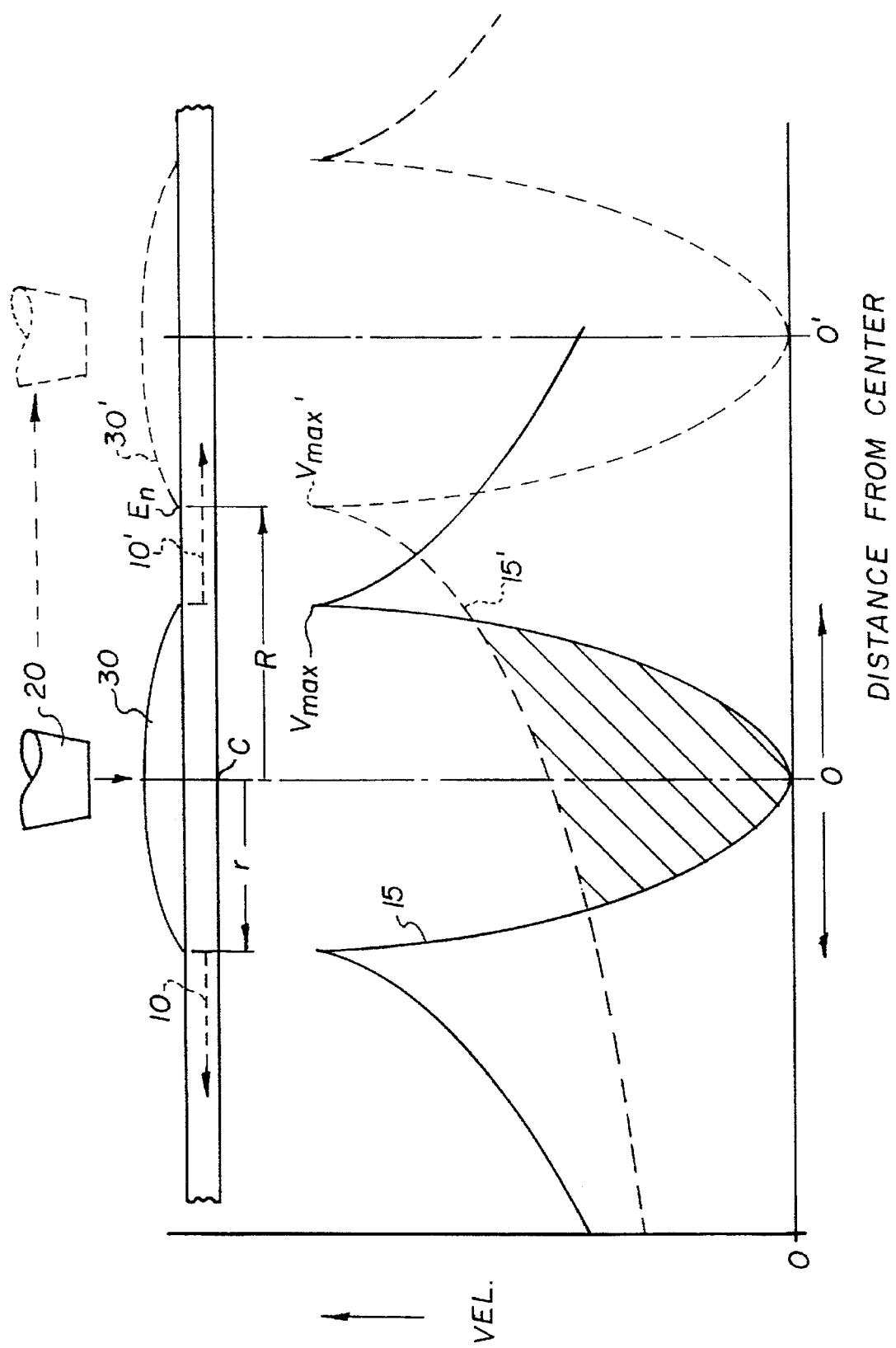
FIG. 2 is a plot of flow velocities within a test element as a function of distance from the center of the contact meniscus.

From FIG. 2, it will be apparent why the instant invention achieves benefits over a wash deposition limited to a single location. That is, when a first wash is dispensed at deposition location "O", the wash under the element surface at the Zero location is substantially nil, with the maximum velocity of wash ($V_{max}$) being at the radius "r" of the meniscus, as shown. As the pool spreads out through the element, arrows 10 and 10', the effect is to provide a wash at a velocity, curve 15, that decreases inversely with increasing distance beyond radius "r", but which is still well above the zero velocity at location "O".

Then, by dispensing another portion of the wash at location "O'" different from location "O", the effect is that the portion of the spreading of the second dispensing, into the element, produces wash velocities (curve 15' shown in phantom) that are effective to wash the area at dispense location "O", in other words, to wash the area under that location with non-zero velocities represented by the shaded area.

This effect can be achieved by providing relative motion between the dispensing tip 20 and the slide element while wash liquid is continually dispensed, hereinafter "continuous moving wash", or by stopping dispensing to allow tip 20 to be moved from location "O" to location "O'" and then continuing the dispensing, hereinafter "discontinuous moving wash". In the former case, there will be a multitude of curves interposed between curve 15 and curve 15', not shown.

In either case, three things are noted:

1) A second amount of wash liquid is deposited at a second location different from the first location of the surface on which the wash liquid is deposited.

2) A variety of speeds of tip movement laterally over the slide test element can be tolerated. Highly preferred, by way of example, are speeds of 0.3 mm/sec.

3) If the dispense rate is other than one using the "ramped method" described above, AND is at a rate in excess of the absorption rate of the slide test element, then it is important, whatever the radius "r" is for the initial meniscus 30, that the near edge $E_n$ of the final meniscus 30', be at a distance R from the center C so that R is $\geq r$. This ensures that peak velocity $V_{max}'$ for the final meniscus will give a thorough wash of the shaded area not washed by meniscus 30. When R=r, then the intersect meniscus edge $E_n$ is displaced 100% of half of the diameter (which is of course radius r) of the meniscus 30. (Alternatively, if the contact meniscus is not perfectly circular, then $E_n$ is preferably displaced 100% of half of the maximum dimension of the contact meniscus, whatever that is.)

It is preferred that the instant invention be combined with the "ramped" method discussed above, to apply the wash first at a dispense rate $R_D$ that is less than the absorption rate $R_A$ of the slide test element, and then to apply it at a rate that exceeds the absorption rate $R_A$. The flow characteristics are slightly different, depending on which of these conditions prevails, and whether the dispensing is a "continuous moving wash" or a "discontinuous moving wash" as defined above.

Considering first the "continuous moving wash", FIGS. 3A–C illustrate the flow characteristics that result over time, that is, while tip 12 is moving and liquid is continuously dispensed, and while proceeding from the condition $R_D<R_A$ to $R_D>R_A$. That is, the initial contact of dispensed liquid L, FIG. 3A, centers at point 0 at time $t_0$, on element E, and produces wash velocity vectors, arrows 40, located at the edges of the meniscus spaced apart a distance "m". This leaves unwashed the shaded portion, FIG. 3B, shown under center point 0. From time t0 to time $t_1$, tip 12 moves, arrow 44, FIGS. 3A and B, to a position slightly adjacent the former position (shown in phantom, FIG. B), centered above point "1" on element E. Because $R_D<R_A$ at this time, substantially all the liquid that contacted element E at time $t_0$, is absorbed into the element, so that a high-speed camera "sees" a new stream of liquid L' approaching an apparently "dry" surface. By the time that stream strikes element E, at time $t_2$, FIG. 3C, tip 12 has moved, arrow 46, to a position directly above center point 2. Importantly, the contact of the liquid produces a meniscus the edge of which gives maximum wash velocity vectors 40',40', one of which moves through the shaded, unwashed area directly underneath center point 0, to wash it.

At this point, $R_D$ is caused to become equal to and then exceed $R_A$. This occurs either by increasing the actual $R_D$ rate, and/or by reason of the fact that the liquid already absorbed by element E, by time $t_2$, produces a reduced rate of absorption $R_A'$ that is $<R_A$ and $<R_D$. Thus, as tip 12 moves on, arrow 48, to the position directly above center point 3, FIG. 3D, the size of the meniscus $m_2$ or contact of stream L with element E, edge to edge, is larger than $m_1$ at time $t_0$. From time $t_3$ on to the cessation of stream L, there is a constant "puddle" of wash liquid on element E that grows in the direction of arrow 50. During these times $t_4, \ldots t_n$ (not shown), tip 12 moves on to subsequent positions adjacent to the right of its position in FIG. 3D, and at any times $t_3, t_4, \ldots t_n$, only a portion of the wash liquid penetrates down in the direction of arrows 40", FIG. 3D (mostly at the edges of the menisci).

Alternatively, FIGS. 4A–D, the wash can be "discontinuous moving wash" as noted above, where dispensing ceases while tip 12 moves to an adjacent position. Parts similar to those described in the previous embodiment have the same reference numeral with the suffix "A". In such a case, FIG. 4A, at the time $t_o$ a drop of wash liquid $L_A$ is deposited from tip 12A, arrow 21, centered on point 0 on element $E_A$ with a contact meniscus of $m_1$. Next tip 12A moves, arrow 44, between depositing, so that at time $t_1$, FIG. 4B, it is centered above point 1 on element $E_A$. At this time, wash liquid $L_A$ starts to be dispensed (shown in phantom), after tip 12A arrives at this location. This cessation of flow between time $t_0$ and $t_1$ in this embodiment is the primary difference from the previously-described embodiment. However, what is the same is that the liquid $L_A$ already on element $E_A$ at time $t_0$, has been absorbed, leaving a shaded column of unwashed volume under point 0, since $R_D<R_A$. By time $t_2$, FIG. 4C, a second, disconnected drop of liquid has contacted element $E_A$ centered at point 2 adjacent to point 1, and some of its maximum velocity wash vectors 40A then act to wash through the shaded region under point 0, as is apparent from FIG. X. By the time $t_n$ is reached when $R_D>R_A$, FIG. 4D, the process is identical to that of the previous embodiment, except that the wash liquid $L_A$ is delivered in discrete amounts because of the tip movement, arrow 48A between dispensing events. (At this time, tip 12A is above center point n, to wash out the shaded region under center point n-1, at least.)

Figure 5:
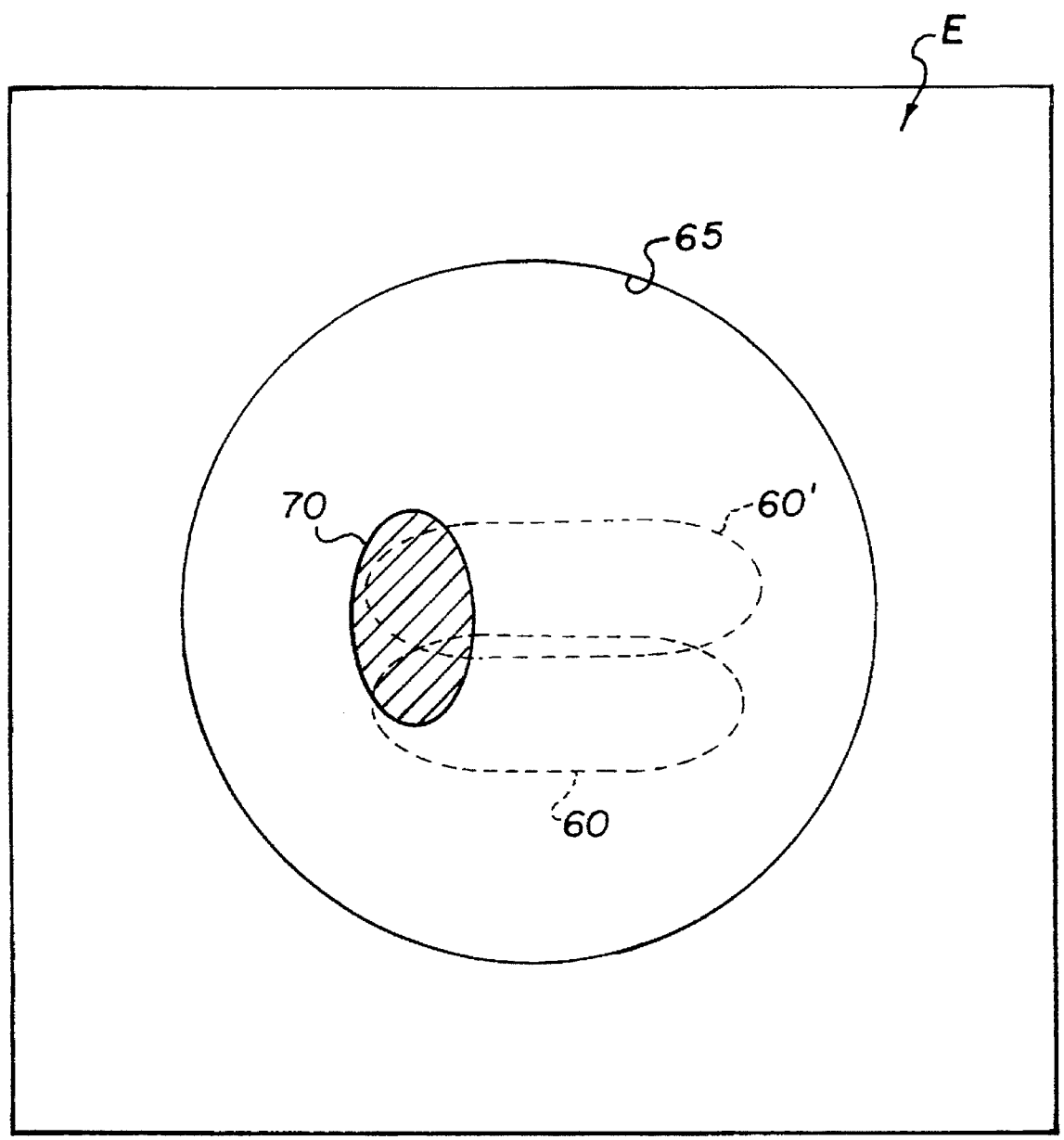
FIG. 5 is a plan view of a slide test element showing the washed area that is obtainable, contrasted with the wash area resulting from a fixed stream.

FIG. 5 illustrates the washed out area that results, as an approximate ellipse 60 or 60'. That is, the ellipse can be anywhere within the open contact circle 65 of element E.

The free indicator that is an interferent to the read process is located along the edges of the ellipse. The ellipse in turn represents the surface area covered by the menisci formed by the moving wash, the menisci overlapping each time contact is made by dispensing from tip 12. Hence, the process of the invention, after washing, comprises reading the bound indicator remaining, in any portion within the ellipse.

In contrast and as a comparison example, FIG. 5 also shows in the shaded area 70, the area that is washed cleanly if ONLY the "ramped" method described in the above-referenced related application is used. It is readily apparent that the useful area for reading is greatly enlarged by the instant method, producing the areas of the ellipses 60 or 60', instead of the area 70. This is not to say area 70 is not useful; it is just not as useful.

Figure 6:
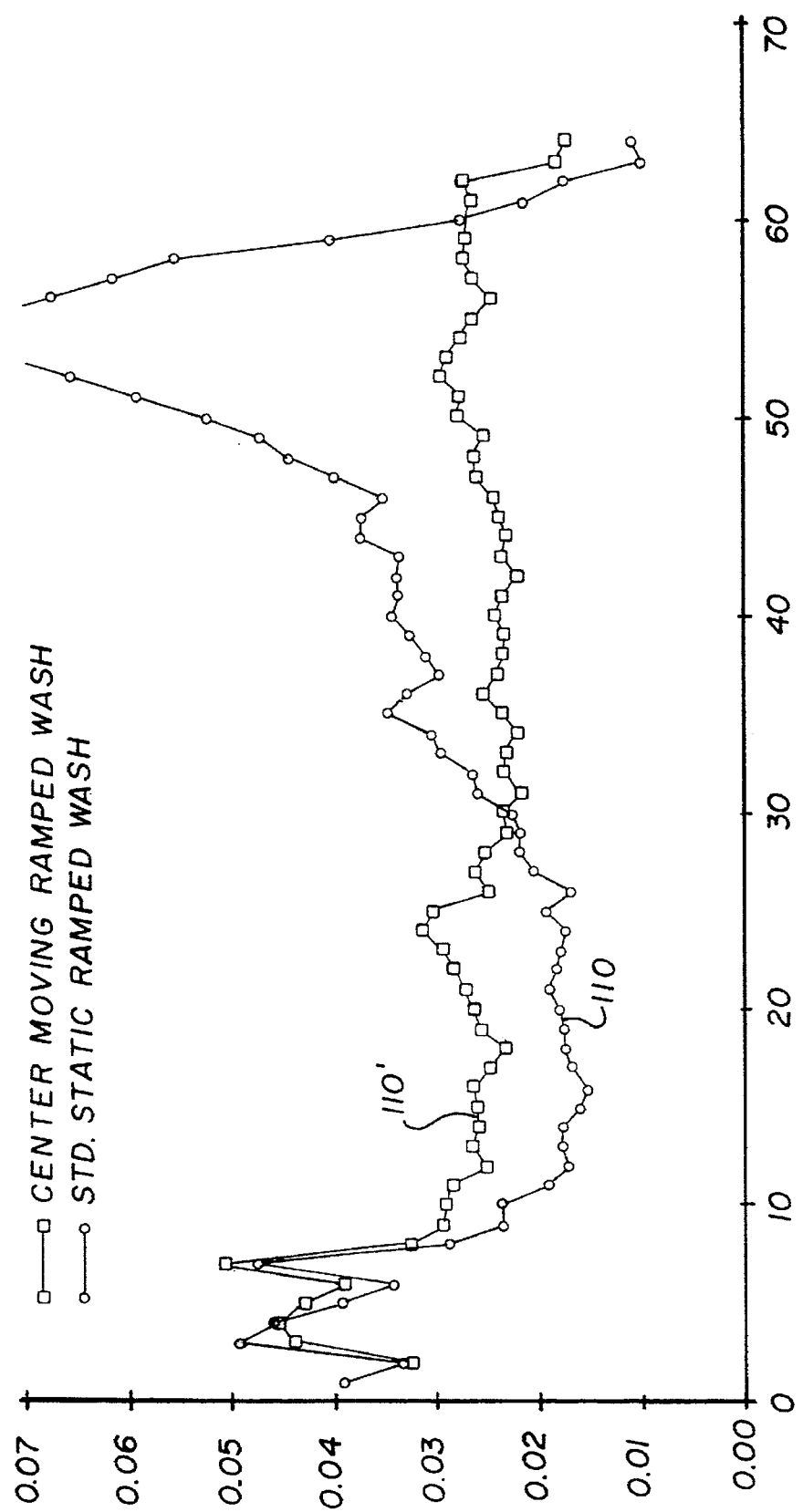
FIG. 6 is a line plot of a center diameter of a mapping of pixels obtained by a scanning of both a test element washed by the "ramped" method, and by the instant invention.
Figure 7:
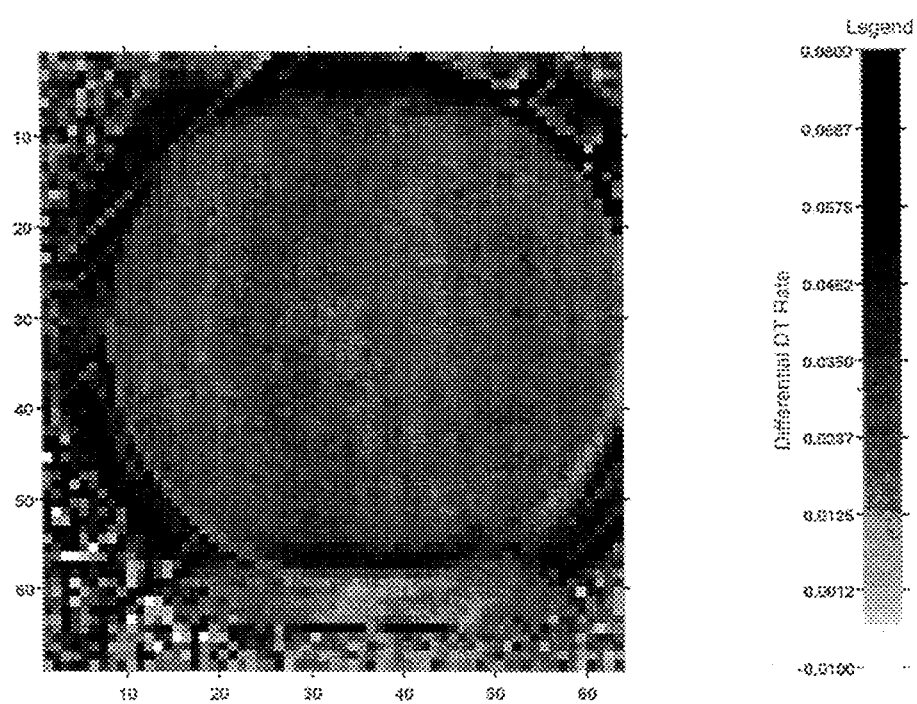
FIGS. 7, 8A and 8B are each a computer mapping in grey scale, using 4×4 grouped pixels, of the differential densities produced by the wash of this invention on a phenobarbital test element, and a ramped wash and the wash of the invention, respectively, on a digoxin test element, all detected at those grouped pixels over a fixed period of time.

FIG. 6 further indicates the difference, measured on a phenobarbital test element available under the trademark 37 Ektachem" from Clinical Diagnostic Systems Inc. In this figure, the trace for the X's, line 110, is that produced by the "ramped" method used alone, with the tip being stationary. The trace for the diamonds, line 110', is the trace for the instant invention. For these traces, the readings are rate readings taken across roughly the center of the reaction area of the test element. FIG. 7 illustrates a plot of pixel values of rates, following the wash treatment of this invention, and it is through this plot, from left to right, that line 110' was taken. The wash solution employed in the experiments, and useful with the invention, had the composition:

| | |
|---|---|
| Hydrogen peroxide | 0.03% |
| Sodium Phosphate (pH 6.8) | 10 mM |
| 4'-Hydroxyacetanilide | 5 mM |
| Diethylenetriaminepentaacetic acid | 10 mM |
| Hexadecylpyridinium chloride | 0.1% |

The wash producing trace 110' used a speed of movement above the slide test element, left to right that was 0.3 mm/sec., and a variable dispense rate as follows: 0.2 microliters/sec for 10 sec., 0.3 microliters/sec for 8 sec., 0.45 microliters/sec for 8 sec., and 0.5 microliters/sec for 4 sec. The same variable dispense rate was used for a pixel plot from which the trace of line 110 was taken, but with the tip fixed in place above the test element.

The variations in rate that are apparent from the traces indicate unwashed areas if the rate does not remain constant. Stated in other words, line plot 110' has a useful read window of from pixel 9 to pixel 32. But most importantly, line 110' produces a useful read window that goes beyond that of trace 110, that is, from pixel 10 to about 60, instead of "just" pixel 32.

Figure 8A:
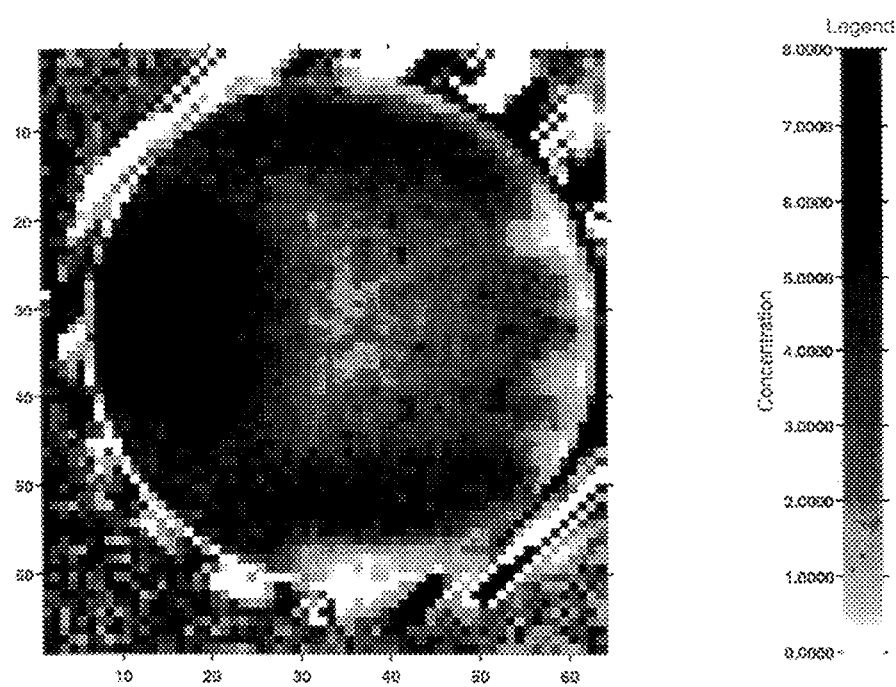
Figure 8B:
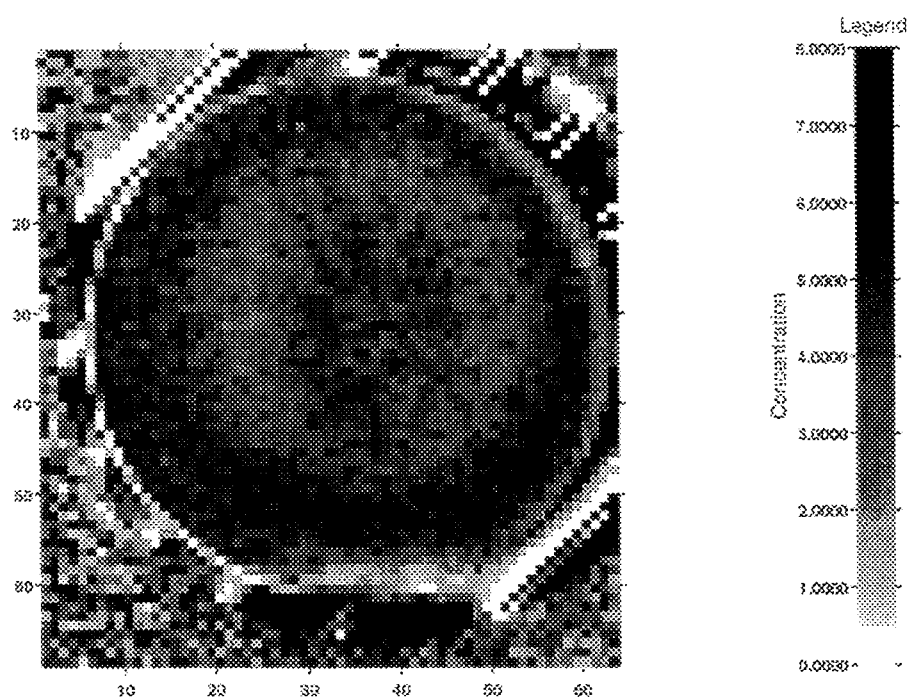

FIGS. 8A and 8B further illustrate by a neutral density photograph, the greater area of test element having a generally uniform read, produced by the instant invention. That is, the small dark area to the left in FIG. 8A is the extent of the washed area using only the "ramped" method of the related Application noted above. In contrast, the much larger area of uniform concentrations shown in FIG. 8B indicates that the wash of the instant invention provides a larger read window.

ALTERNATIVE EMBODIMENTS

As in the case of the aforesaid related application Ser. No. 393,632, this invention facilitates the use of a dual wash, that is, washing twice the same test element, if such should be desired, regardless of the composition of such dual washes. However, it is conventional in a dual wash to leave out active reagents, such as hydrogen peroxide, in the first wash, but include all desired reagents in the second one. This invention, by reason of the movement of the stream laterally over the surface area of the slide test element, causes a reduction in the impact of the two successive dispensing streams onto the top layer. That top layer can in extreme cases experience degradation if the wash stream remains static (fixed) as is done with the "ramped" method, AND has to be done twice. Thus the invention makes dual washing more feasible than is the case where the wash is a fixed stream.

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. In a method of separating bound labeled indicator from free labeled indicator in a layer of a test element for immunoassay, the method comprising
   a) depositing sample containing a target immunoanalyte capable of binding to said labeled indicator or to an immobilized antibody in competition with said labeled indicator, onto an exterior surface of a test element in the presence of said labeled indicator and
   b) adding an amount of wash liquid to said exterior surface to form a pool of the liquid having a meniscus on said surface, the liquid penetrating said surface over a read area bounded by a closed intersect edge formed between said pool meniscus and said surface, so that penetrating liquid can push free labeled indicator away from bound labeled indicator in a portion of said layer below said bounded area,
   the improvement wherein said step b) comprises i) depositing a first amount of wash liquid at a first location on said surface in a pool, (ii) allowing at least a portion of said pool to spread out through a first portion of said test element to wash out free labeled indicator, and then (iii) depositing a second amount of wash liquid at a second location on said surface different from said first location to spread out through a second portion of said test element different from said first portion, so that said intersect edge is displaced over said surface over time and the liquid flowing into said test element at said intersect edge sweeps through more of said read area than is the case when washing from only said first location, thus reducing background signal due to non-separated free labeled indicator remaining in said portion of said layer below said bounded area.

2. A method as defined in claim 1, wherein said intersect edge is displaced by at least 100% of half of the maximum-dimension of said pool intersect edge occurring when washing from only said first location.

3. A method as defined in claim 1 or 2, and thereafter reading the bound indicator in a portion of said layer that is coextensive with at least part of said layer portion below said bounded area.

4. A method as defined in claim 1, wherein said step iii) is delayed from step ii) until all liquid has soaked into said element from said pool formed by said step i).

5. A method as defined in claim 1, wherein said step (iii) occurs while a portion of the pool formed from step (i) still remains on said surface.

6. A method as defined in claim 1, wherein said step b) comprises providing relative motion between the source of wash liquid and said test element while the wash liquid is being dispensed.

* * * * *